Figure 1:
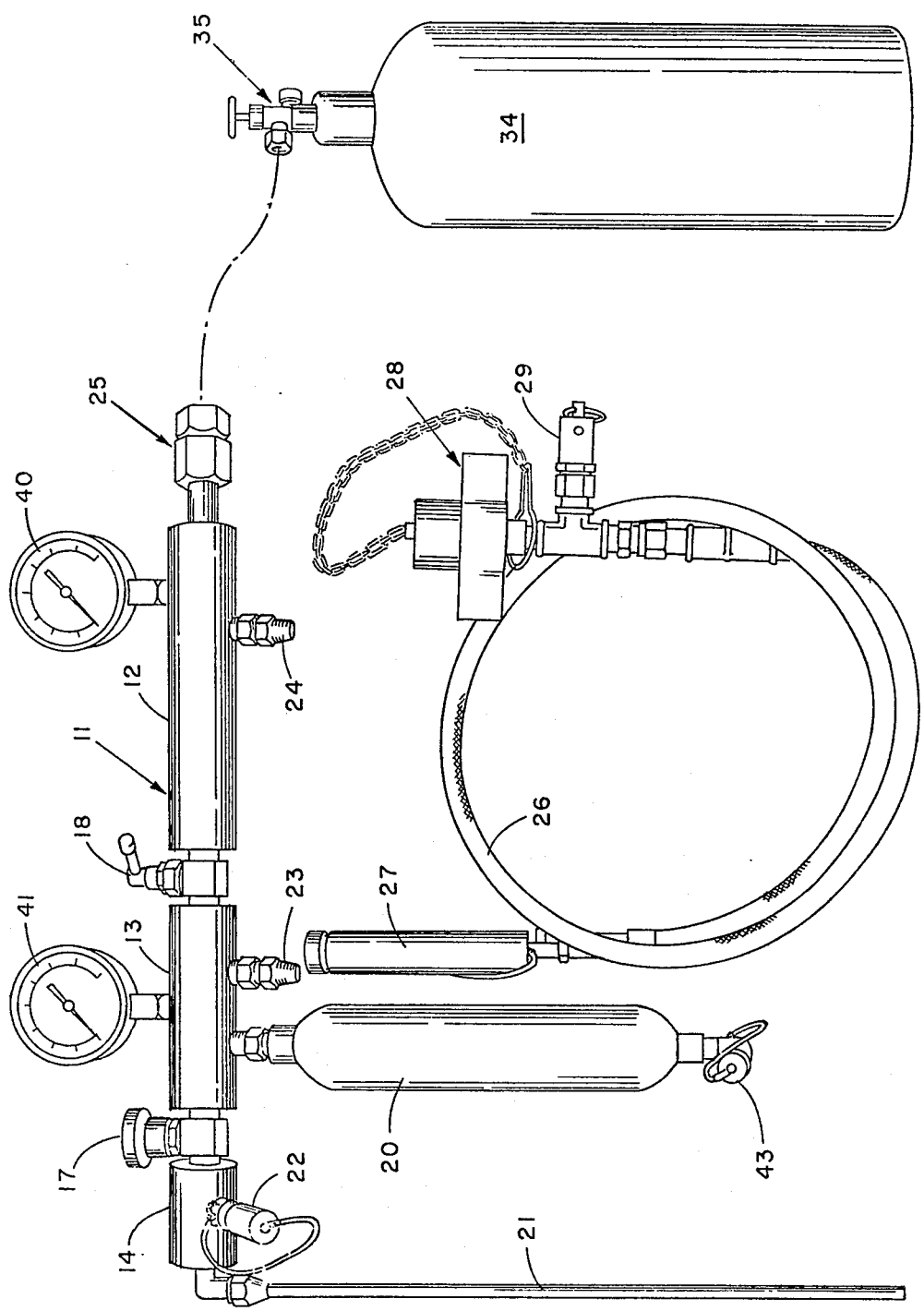

United States Patent [19]

Pecor

[11] 4,173,895
[45] Nov. 13, 1979

[54] APPARATUS FOR AND METHOD OF SAMPLING LIQUID OXYGEN

[76] Inventor: Lloyd A. Pecor, 502 Sparks Dr., Grand Prairie, Tex. 75051

[21] Appl. No.: 926,294

[22] Filed: Jul. 20, 1978

[51] Int. Cl.² ........................ G01N 1/10; G01N 1/22
[52] U.S. Cl. ............................ 73/421.5 R; 73/422 R; 141/48
[58] Field of Search .......... 73/421 R, 421 B, 421.5 R, 73/422 R; 141/48, 49, 95

[56] References Cited

U.S. PATENT DOCUMENTS

| 3,123,982 | 3/1964 | Brown et al. | 73/421.5 R |
| 3,272,238 | 9/1966 | Groppe | 141/48 |
| 3,544,276 | 12/1970 | Merwitz, Sr. | 73/421.5 R |

*Primary Examiner*—S. Clement Swisher
*Attorney, Agent, or Firm*—Roylance, Abrams, Berdo & Farley

[57] ABSTRACT

An apparatus for sampling liquid gas with minimum contamination includes a manifold assembly separated into three sections by two valves and having a vent at one end and a fitting for connecting a gaseous sample container to the apparatus at its other end. A liquid sample receiving cylinder is connected to the middle section of the manifold assembly. A flexible conduit, which may be connected to a unit to be sampled at one end, may be selectively coupled to the sample receiving cylinder or the first section of the manifold assembly for purging the service hose. The method of using this apparatus includes purging sections of the manifold, receiving cylinder and flexible conduit with residual gas vapor pressure in a sample container, purging the flexible conduit with liquid gas from a unit to be sampled, filling the receiving cylinder with liquid gas, and converting the liquid gas to a gaseous state in the sample container.

11 Claims, 2 Drawing Figures

APPARATUS FOR AND METHOD OF SAMPLING LIQUID OXYGEN

This invention relates to an apparatus for and method of obtaining a sampling of liquid gas with a minimum of contamination.

Existing methods of obtaining a sample of liquid oxygen which is to be analyzed include drawing the liquid and converting it to a gas to determine its purity. These methods require rigorous cleaning and purging procedures. The systems presently available for reducing equipment contamination in these procedures to an acceptable level are extremely costly in terms of unnecessary waste of the liquid oxygen due to untrue analysis reports. The liquid oxygen is wasted in draining the liquid from its container, purging and refilling the unit, transferring the sample to a laboratory and returning the sample, as well as other steps. It has been determined that the cost of obtaining the test of one sample repeated 18 times is $7,483. This cost becomes $14,400 where an existing closed-looped sampler is used.

The presently existing sampling systems are deficient in that atmospheric contamination occurs through the bore of the liquid oxygen cylinder nipple between the time that a valve/adaptor section is removed and replaced. The present invention avoids this and other deficiencies by providing a closed-loop assembly which obviates atmospheric and other contamination of the sample.

Accordingly, it is an object of the present invention to provide an apparatus and method for obtaining a sample of liquid oxygen easily with a minimum of contamination. Specifically, it is the object of the present invention to obtain a sampling of liquid oxygen without exposing the sample to contamination from ambient atmospheric sources.

Another object of this invention is to provide an apparatus and method of attaining a sample of liquid gas wherein the samples are withdrawn through a close loop system and transferred to a sample container within the same system.

A further object of the present invention is to provide a method and apparatus in which the dispensing equipment is automatically purified at the taking of each sampling so that it is immediately available for subsequent samplings.

Yet another object of the present invention is to provide an apparatus and method which reduces the possibilities of injuries due to escaping liquid and the associated dangers.

Yet a further object of the present invention is to provide a method and apparatus for taking liquid gas samples which results in substantial savings through reduced maintenance time.

The foregoing objects are obtained by an apparatus which includes a manifold assembly separated in three separate sections by two valves and having a vent on the end adjacent the first section and a liquid or sample container coupling at the end adjacent the third section, a conduit purge connector attached to the first section, a sample receiving cylinder having one end coupled to the second section and its other end supporting a conduit fitting, and a flexible conduit having a quick disconnect fitting at one end connectable to either the conduit purge connector or the conduit fitting and a unit coupling at the other end; and a method which includes using the above apparatus and involves purging the second and third sections, the sample receiving cylinder and the flexible conduit with residual gas vapor pressure from a sample container, purging the flexible conduit with liquid gas from a unit to be sampled, filling the receiving cylinder with liquid gas from the unit through the flexible conduit, allowing the liquid to convert to a gas in the manifold.

The samples obtained by the apparatus and method of the present invention are free of atmospheric contaminants and are obtained routinely through observation of the method. The method and apparatus of the present invention also achieve substantial savings through reduced transportation requirements in that less samples need be sent to appropriate testing stations thereby also decreasing the time for processing of additional samples. These savings result in an increased availability of aircraft or other operating equipment which is dependent upon mandatory, thorough samples of oxygen or other liquids.

Other objects, advantages, and salient features of the present invention will become apparent from the following detailed description, which when taken in conjunction with the annexed drawings, discloses preferred embodiments of the present invention.

Figure 2:
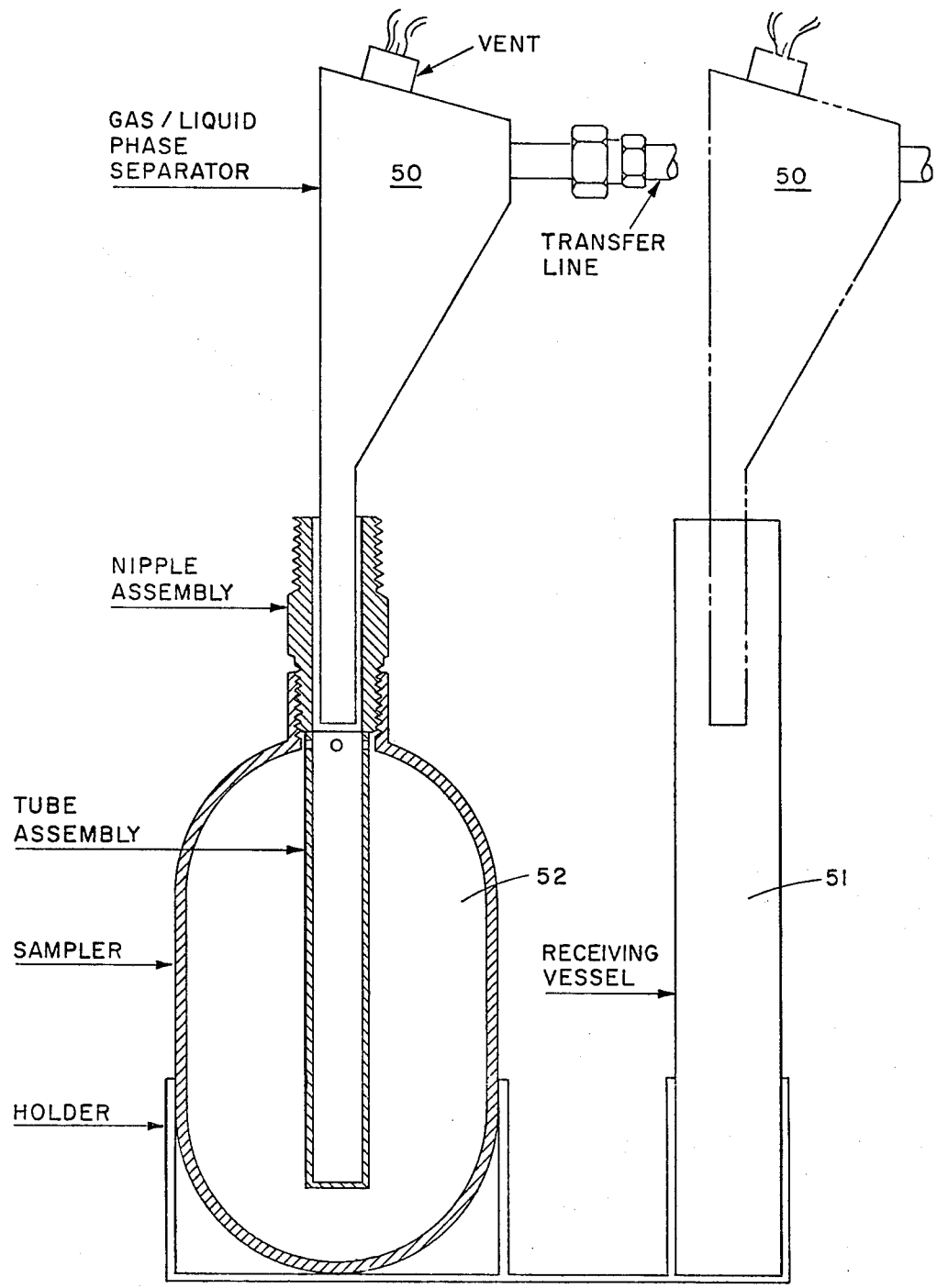

Referring to the drawings, which form a part of this specification:

FIG. 1 is a side elevation graphically illustrating the components of the apparatus of the present invention; and FIG. 2 is a side elevation, partial ensectioned, graphically illustrating a conventional system for obtaining a sample of liquid oxygen.

Referring to FIG. 1, the apparatus of the present invention includes a manifold assembly 11 divided into three sections, 12, 13 and 14. A bellows valve 17 is provided between the sections 13 and 14 for controlling the passage of fluid therebetween. A toggle valve 18 is provided between sections 13 and 12 for controlling the flow of fluid therebetween.

A vent pipe 21 extends from an end of section 14 remote from the valve 17. A conduit purge connector 22 is also provided on the section 14.

The section 13 includes a pressure guage 41 for monitoring the fluid pressure therein, a relief valve 23, and a 300 cc liquid sample receiving cylinder 20. One end of the sample receiving cylinder 20 is detachably coupled to the section 13. The other end of the same receiving cylinder 20 has a conduit fitting 43.

The section 12 includes a guage 40 for monitoring the pressure therein, a sample cylinder coupling 25 and a relief valve 24.

A flexible hose 26 provides a flexible conduit and has a quick disconnect fitting 27 at one end and a unit coupling 28 at its other end. A relief valve 29 is provided in the hose 26 adjacent the unit coupling 28. The quick disconnect fitting may be selectively coupled to the conduit purge connector 22 or the conduit fitting 43.

A sample gaseous cylinder container 34 may be coupled to the manifold assembly through the sample container coupling 25. A valve fitting 35 is provided on the container 34 for controlling the flow of fluid into and out of the container 34 and for accommodating connection with the gaseous sample container 34 coupling 25 by a conventional hose depicted graphically in FIG. 1. The container 34 contains residual gas which is used to purge the unit prior to use of the unit.

In operation, the valves 17, 18 are initially opened. The valve 35 of the sample gaseous container 34 is then coupled to the container coupling 25 when the valve 35 is closed. The quick disconnect fitting 27 is coupled to the fitting 43 on the sample liquid receiving cylinder 20. After the bellows valve 17 is closed, the valve fitting 35 is opened to enable the residual gas vapor pressure in the sample container 34 to purge the sections 12, 13, the liquid sample receiving cylinder 20 and the conduit 26 of outside air.

To purge the conduit 26, of gas the quick disconnect fitting 27 is removed from the fitting 43 and coupled to the hose purge connector 22. The unit coupling 28 is then connected to a unit to be sampled (not shown). After these connections have been made, a pressure of 25 to 35 psi is created in the unit and liquid gas is allowed to flow from the unit through the conduit 26 and the section 14 until liquid appears at the end of the vent pipe 21. This insures that there is only liquid gas in conduit 26 and fitting 27.

To fill the liquid sample receiving cylinder 20, the valve 17 is opened, the valve 18 is closed, and the quick disconnect fitting 27 is replaced on the fitting 43 of the sample receiving cylinder 20. Liquid from the unit is then allowed to flow through the conduit 26 and into the receiving cylinder 20 until a liquid appears at the end of the vent pipe 21 to indicate that the sample receiving cylinder is filled. This insures that there is only liquid gas in the cylinder 20.

At this time, the flow of liquid gas into the sample receiving cylinder 20 is halted. After the valve 17 is closed and the valve 18 is opened, the liquid gas is converted to a gaseous state and pressure is permitted to build up in the manifold assembly sections 12 and 13 and in the gaseous sample container 34 to approximately 300 psi. Then, the valve fitting 35 on the sample container 34 is closed, the valves 17, 18 are opened to relieve pressure in the manifold assembly 11 and receiving cylinder 20. After pressure has been relieved, the sample container 34 may be removed from the manifold assembly 11 and the manifold assembly 11 may be capped.

The above procedure for obtaining a sample of liquid substantially free of contamination by the equipment used is a marked improvement over current methods of taking samples. One common current method is shown in FIG. 2 and requires the use of a gas/liquid phase separator 50 which is first inserted into a receiving vessel 51 for cooling down and purging, and then inserted into a sampler 52. One major deficiency in this operation is the possibility of high concentration of atmospheric contamination which can be admitted through the bore of the sampler nipple assembly between the time a valve/adaptor is removed from and replaced on the sampler.

Although the invention has been described in considerable detail with particular reference to a certain preferred embodiment thereof, variations and modifications can be effected within the spirit and scope of the invention as described hereinbefore, and as defined in the appending claims.

What is claimed is:

1. An apparatus for sampling liquid gas with minimum contamination comprising
   a manifold assembly having a vent at one end and a sample container coupling at the other end; said manifold assembly including a first section adjacent said vent, a second section and a third section adjacent said sample container coupling, said second section being located between said first and third sections;
   a first valve between said first and second sections;
   a second valve between said second and third sections;
   a conduit purge connector attached to said first section;
   a sample receiving cylinder coupled at one end to said second section, the other end of said cylinder having a conduit fitting; and
   a flexible conduit having a quick disconnect fitting at one end and a unit coupling at its other end; said quick disconnect fitting adapted to be selectively connected to said conduit fitting and said conduit purge connector.

2. An apparatus according to claim 1, wherein pressure indicating means are coupled to each of said second and third sections.

3. An apparatus according to claim 1, wherein a relief valve is provided in each of said second section, said third section and said conduit.

4. An apparatus according to claim 1, wherein a sample container is detachably connected to said sampler container coupling through a valve on said sample container.

5. An apparatus according to claim 1, wherein said vent comprises a vent pipe.

6. A method of obtaining a gas sample with minimum contamination using an apparatus having a manifold assembly with a vent at one end and a sample container coupling at the other end, the manifold assembly being divided into three sections with a first valve between the first and second sections and a second valve between the second and third sections, the first section including the vent and a conduit purge connector, the third section including the sample container coupling, a sample receiving cylinder with one end thereof coupled to the second section and the other end supporting a conduit fitting, and a flexible conduit with a quick disconnect fitting at one end and unit coupling at the other end; comprising
   a first step of purging the second and third sections, the sample receiving cylinder and the flexible conduit;
   a second step of purging the first section and the flexible conduit of gas;
   a third step of filling the receiving cylinder with liquid gas from a unit to be coupled;
   a fourth step of allowing the liquid to convert to a gas in the manifold assembly and allowing the pressure to build up in the manifold assembly and a sample container connected to the sample container coupling; and
   a fifth step of relieving pressure in the manifold and sample receiving cylinder and removing the sample container from the manifold assembly.

7. A method according to claim 6, wherein said first step comprises
   opening the first and second valves;
   coupling a valve of a sample container to the sample container coupling when the sample container valve is closed;
   connecting the conduit quick disconnect fitting to the receiving cylinder conduit fitting;
   closing the first valve; and
   opening the sample container valve to enable residual gas vapor pressure in the sample container to purge the second and third sections, the receiving cylinder and the conduit.

8. A method according to claim 6, wherein said second step comprises
closing the first valve;
connecting the conduit quick disconnect fitting to the conduit purge connector on the first secion;
connecting a unit from which a sample is to be taken to the unit coupling on the conduit;
allowing liquid gas to flow from the unit through the conduit and first section until a liquid appears at the vent.

9. A method according to claim 6, wherein said third step comprises
opening the first valve;
closing the second valve;
connecting the quick disconnect fitting on the conduit to the conduit fitting on the receiving cylinder;
allowing liquid to flow from a unit connected to the unit coupling on the conduit into the receiving cylinder until liquid appears at the vent.

10. A method according to claim 6, wherein said fourth step comprises
stopping flow of liquid gas into the receiving cylinder;
closing the first valve;
opening the second valve; and
permitting pressure to build up in the manifold assembly and the sample container to be filed.

11. A method according to claim 6, wherein said fifth step comprises
closing a valve on the sample container to close same;
opening said first and second valves to relieve pressure in the manifold assembly and receiving cylinder; and
removing the sample container from the manifold assembly and capping the manifold assembly.

* * * * *